(12) United States Patent
Nowak et al.

(10) Patent No.: US 7,485,472 B2
(45) Date of Patent: Feb. 3, 2009

(54) SIMPLE METHOD FOR QUANTITATIVE MEASURING THE ADHESION OF PLATELETS EX VIVO

(75) Inventors: Gotz Nowak, Erfurt (DE); Elke Bucha, Erfurt (DE)

(73) Assignee: JenAffin GmbH, Jena (DE)

( * ) Notice: Subject to any disclaimer, the term of this patent is extended or adjusted under 35 U.S.C. 154(b) by 430 days.

(21) Appl. No.: 10/344,359

(22) PCT Filed: Aug. 9, 2001

(86) PCT No.: PCT/DE01/03041

§ 371 (c)(1),
(2), (4) Date: Aug. 7, 2003

(87) PCT Pub. No.: WO02/12885

PCT Pub. Date: Feb. 14, 2002

(65) Prior Publication Data

US 2004/0029193 A1     Feb. 12, 2004

(30) Foreign Application Priority Data

Aug. 9, 2000  (DE) .............................. 100 38 900

(51) Int. Cl.
*G01N 33/544* (2006.01)

(52) U.S. Cl. .................. 436/529; 436/524; 436/527; 436/534; 436/10; 436/17; 436/18; 436/63; 436/69; 436/165; 435/2; 435/286.7; 422/73

(58) Field of Classification Search ............... 435/2, 435/7.21, 286.5, 286.7; 436/523–534, 539, 436/10, 17, 18, 63, 69, 165; 422/73
See application file for complete search history.

(56) References Cited

U.S. PATENT DOCUMENTS 5,576,185 A * 11/1996 Coulter et al. ............. 435/7.23
5,773,228 A    6/1998 Reed et al. ................. 435/7.21

FOREIGN PATENT DOCUMENTS

WO   WO97/18474   5/1997

OTHER PUBLICATIONS

Bonnefoy et al., Efficiency of Platelet Adhesion to Fibrinogen Depends on both Cell Activation and Flow, Biophysical Journal, 78: 2834-2843 (Jun. 2000).*
Bombeli et al., Adhesion of Activated Platelets to Endothelial Cells: Evidence for a GPIIbIIIa-dependent Bridging Mechanism and Novel Roles for Endothelial Intercellular Adhesion Molecule I (ICAM-1), $\alpha v \beta 3$ Integrin, and GPIb$\alpha$, J. Exp. Med. 187 (3): 329-339 (Feb. 2, 1998).*

* cited by examiner

*Primary Examiner*—Gailene R Gabel
(74) *Attorney, Agent, or Firm*—Kagan Binder, PLLC

(57) ABSTRACT

The invention relates to measuring of the adhesion of platelets ex vivo. In this method, monodisperse polymer particles are added to blood, and the number of platelets in the blood are measured before and after shaking of the sample. The level of adhesion of the platelets is determined by comparing the number of platelets prior to shaking with the number of platelets after shaking. Methods of establishing an adhesion index and diagnosis of a patient are also provided.

12 Claims, No Drawings

SIMPLE METHOD FOR QUANTITATIVE MEASURING THE ADHESION OF PLATELETS EX VIVO

The thrombogenicity of arterial occlusive diseases and the predisposition thereof is determined by means of pathological platelet reactions. The blood platelet-directed starter reaction for manifest arterial macro and micro thromboses is focus for a range of drug developments. In recent years, the therapeutic principle of blocking GPIIb/IIIa receptors of platelets has shown to be particularly promising. In various studies (Capture, Epilog, Epic, Epistent and others), it could be demonstrated without doubt that a thrombotic reaction can be prevented or antagonised by means of substances obstructing fibrinogen receptors of the platelets (GPIIb/IIIa). So far, the greatest experience has been gained with a monoclonal antibody fragment, the so called Abciximab (Reopro™), but also further substances from other sources, such as natural disintegrines or peptide antagonists or peptidomimetica are being subjected to clinical examination at present.

In practice, the essential problem with these substances is the fact that they exhibit clinical efficiency only when 60-80% of the GPIIb/IIIa receptors of all platelets in circulation are blocked. The extremely low therapeutic index of these substances is to be explained by the fact that already at 90-95% receptor blocking, there is an excessive bleeding tendency.

This severe side effect also limits a broad application of this new substance group. In the past, there were plenty of attempts to control the blood level by means of the most varied methods determining the function of the platelets. However, there is no correlation between the blood level of the GPIIb/IIIa antagonists and the effect, since there is no direct relationship between the height of the substance blood level and the strength of the aggregation inhibition. This lack of correlation is, above all, due to the variable number of circulating platelets but also the number of the integrin molecules exposed at the platelet surface. Mostly, methods for measuring the platelet aggregation are used for the detection of the efficacy. The aggregation agonists reactions carried out in plasma containing platelets or platelet-rich plasma for collagenes or ADP are time-consuming and costly and show the real conditions in the blood of the patient only indirectly, since they do not allow reactions that are identical to natural reactions due to the obligatory separation and enrichment of the plasma of the patient with blood platelets.

A POCT-capable whole blood method of platelet aggregation, the ultegra accumetics method, has too great a scattering effect in the therapeutic-toxic range of the GPIIb/IIIa receptor antagonists and is extremely cost-intensive. This method, too, uses a strong aggregation trigger as measuring principle. Furthermore, analyses of clotting global tests, such as thrombelastographies and prothrombin time, vary too much so that determination of the percentage inhibition level of the platelet function for these tests can hardly be anticipated.

Thus, the problem of the invention is to overcome the above-mentioned disadvantages of the state of the art. This problem has been solved by the surprising finding that specific polymer surfaces are an ideal adhesion area for platelets.

The platelet adhesion and platelet spreading test known so far are qualitative methods using microscopy that take place on glass slides. The method introduced herein uses glass-like polymers that have been made into specific micro particles with "rough" surfaces. These micro particle surfaces are the direct adhesion partners for activated platelets. By means of addition of a defined quantity of monodisperse polymer particles to anticoagulated whole blood and short incubation by shaking at room temperature, an adhesion index can be determined by measuring the difference of the number of platelets in the suspension before and after shaking of the polymer particle. The method introduced herein is designed in such a way that said adhesion index is 50 (50±8) with patients and probands without coagulation defect. In the case of adhesion inhibition after treatment with GPIIb/IIIa receptor antagonists, a reduced adhesion occurs which is strictly dose-dependent; in this case the adhesion index would be <40. Moreover, this test can also be used to determine an increased platelet adhesion in patients.

Thus, the invention relates to the use of defined amounts of monodisperse particles obtained from natural and artificial polymers. The particles used can consist both of human plasma proteins and of monodisperse polymer particles with a diameter between 1 and 20 µm, preferably between 1 and 10 µm, most suitably monodisperse porous particles of a size of 5-6 µm of polyphenylmethacrylate. The auxiliary materials used for the quantitive adhesion method simply are a small shaker (M51 by IKA) and a blood cell counting device, such as e.g. the device Celldyn 1600 by Abbott or similar blood cell analysers, as used in every clinical chemical laboratory. Within 15 min, the corresponding data can be obtained. The method can be carried out directly at the sick bed or at the heart-circulation-function measuring place. The method has POCT quality, does not depend on the number of the circulating platelets (80,000-400,000 platelets/µl) and is not influenced by variations of the fibrinogen levels (1-5 g/l) either.

Formulation: 0.2 ml anticoagulated blood e.g. citrate blood (1/10 v/v)

+0.002 ml 5% particle suspension shake for 10 min at 600/min a) determination of the number of platelets before shaking b) determination of the number of platelets after shaking $$AI \text{ (adhesion index)} = \frac{\text{(number of platelets before shaking)} - \text{(number of platelets after shaking)}}{\text{(number of platelets before shaking)}} \times 100$$

The invention claimed is:

1. A diagnostic method for measuring the adhesion of platelets ex vivo comprising
    a) selecting an amount and type of monodisperse polymer particles derived from at least one artificial polymer;
    b) providing a sample of whole blood;
    c) adding said monodisperse polymer particles to the sample of whole blood to form a blood/polymer particles composition;
    d) measuring the number of platelets in the whole blood/polymer particles composition;
    f) shaking the whole blood/polymer particles composition to allow platelets in the whole blood to adhere directly to the surface of the polymer particles;
    g) measuring the number of platelets in the whole blood/polymer particles composition after shaking that remain in suspension in the composition; and
    h) determining the percent level of adhesion of the platelets by comparing the number of platelets in suspension prior to shaking with the number of platelets in suspension after shaking.

2. The method of claim 1, wherein the artificial polymer is polyphenylmethacrylate.

3. The method of claim 2, wherein the artificial polymer is porous.

4. The method of claim 1 wherein the polymer particles have a diameter of 1 to 20 μm.

5. The method of claim 4 wherein the diameter is 1 to 10 μm.

6. The method of claim 5 wherein the diameter is 5 to 6 μm.

7. The method of claim 1, wherein the measuring step is a step in a process of carrying out a diagnosis of increased or reduced adhesivity of platelets, ex vivo.

8. The method of claim 1, wherein the measuring step is a step in a process of monitoring the effect of substances inhibiting platelet function in the whole blood of a patient.

9. The method of claim 1, wherein the measuring step is a step in a process of monitoring the effect of GPIIb/IIIa receptor antagonists on platelet function in the whole blood of a patient.

10. The method of claim 1, wherein prior to the adding polymer particles step, the whole blood has been treated with an anticoagulant.

11. The method of claim 1, wherein prior to the adding polymer particles step, the whole blood has been treated with a GPIIb/IIIa receptor antagonist.

12. The method of claim 1, wherein the measurement of the number of platelets in suspension is carried out by using a blood cell counting device.

* * * * *